(12) United States Patent
Liu et al.

(10) Patent No.: US 12,318,162 B2
(45) Date of Patent: Jun. 3, 2025

(54) DEVICE

(71) Applicant: PRECISION ROBOTICS LIMITED, London (GB)

(72) Inventors: Jindong Liu, Isleworth (GB); Joshua Arieh Shenker, Borehamwood (GB)

(73) Assignee: PRECISION ROBOTICS LIMITED, London (GB)

( * ) Notice: Subject to any disclaimer, the term of this patent is extended or adjusted under 35 U.S.C. 154(b) by 383 days.

(21) Appl. No.: 17/799,657

(22) PCT Filed: Feb. 9, 2021

(86) PCT No.: PCT/GB2021/050291
§ 371 (c)(1),
(2) Date: Aug. 13, 2022

(87) PCT Pub. No.: WO2021/161002
PCT Pub. Date: Aug. 19, 2021

(65) Prior Publication Data
US 2023/0074912 A1 Mar. 9, 2023

(30) Foreign Application Priority Data
Feb. 13, 2020 (GB) ..................... 2001990

(51) Int. Cl.
*A61B 34/37* (2016.01)
*A61B 34/00* (2016.01)

(52) U.S. Cl.
CPC .............. *A61B 34/70* (2016.02); *A61B 34/37* (2016.02)

(58) Field of Classification Search
CPC ................................ A61B 34/70; A61B 34/37
See application file for complete search history.

(56) References Cited

U.S. PATENT DOCUMENTS

| | | | | |
|---|---|---|---|---|
| 4,990,839 A | * | 2/1991 | Schonlau | B25J 9/161 318/568.17 |
| 6,587,750 B2 | * | 7/2003 | Gerbi | A61B 34/70 600/595 |
| 8,219,245 B2 | * | 7/2012 | Merk | B25J 9/102 700/250 |
| 8,306,661 B2 | * | 11/2012 | Ueyama | B25J 9/1697 348/94 |
| 9,126,332 B2 | * | 9/2015 | Caron | B25J 9/08 |
| 9,321,172 B2 | * | 4/2016 | Johnson | H02K 11/25 |
| 9,545,288 B2 | * | 1/2017 | Morash | A61B 34/30 |

* cited by examiner

*Primary Examiner* — Rina I Duda
(74) *Attorney, Agent, or Firm* — HSML P.C.

(57) ABSTRACT

An arm device comprising a universal joint, which universal joint comprises a first wrist joint, a second wrist joint and a first elbow joint wherein: each wrist joint comprises a first part, a second part and a slipring, which slipring comprises a rotor coupled to the first part and a stator coupled to the second part, which rotor is coaxially engageable with the stator and infinitely rotatable relative to the stator such that: the first part of the first wrist joint is infinitely rotatable relative to the second part of the first wrist joint about a first axis, and the first part of the second wrist joint is infinitely rotatable relative to the second part of the second wrist joint about a second axis; the first elbow joint comprises a first portion and a second portion, which first portion is rotatably engageable with the second portion about a third axis; the first wrist joint is coupled to the first elbow joint; and first elbow joint is coupled to the second wrist joint.

19 Claims, 10 Drawing Sheets

DEVICE

The present application relates generally to an arm device for controlling a robot, and specifically, but not exclusively, to an arm device forming part of a robotic surgical device. The present application also relates to a joint forming part of such an arm device.

In order for a robot with multiple degrees of freedom to be controlled intuitively by an operator, a master controller may be used which captures the operator's hand gestures and can then translate them as commands to the slave robot.

One example application in which robots with multiple degrees of freedom are controlled by an operator using such master controllers is medical surgery. Surgical robots are being used for an increasing number of minimally invasive surgical procedures due to the manoeuvrability and dexterity they offer while operating with minimal incisions that lead to reduced scarring and recovery times.

Ideally, a master controller should provide an operator with complete and unrestricted movement of the controller with their hand which should in turn translate to accurate control of the slave robot.

Known master controllers comprise joints with a plurality of rotational axes in order to measure the orientation and position of the operator's hand.

In particular, known master controllers comprise a joint, or combination of joints, with three axes of rotation that are normal to one another in order to measure the pitch, yaw and roll angle of the operator's hand. However, when any two of the rotational axes align and become parallel, coaxial or overlap the operator may experience a motion-lock feeling, known more commonly as "gimbal-lock", because one degree of freedom is "lost" in such a situation.

The occurrence of gimbal lock can be a problem for a surgeon operating a master controller for a slave robot as it can limit the freedom of movement and force them to move in a way that is not ideal during surgery. This issue would typically be especially prevalent in systems that utilise passive joints where it is not possible to actively bias against gimbal lock. Therefore, known master controllers comprise active joints which are able to actively bias against the occurrence of gimbal lock.

A disadvantage of active joints is that the bias against gimbal lock may force the surgeon to move their hand in a way not optimal during the surgical procedure they are performing. In extreme circumstances this could cause harm to the patient. Another disadvantage is that the addition of a motor to provide a bias against gimbal lock makes the master controllers bulky and more expensive.

Therefore it would be beneficial to provide a master controller with passive joints where the risk of gimbal lock is reduced as much as possible.

According to a first aspect of the invention, there is provided an arm device comprising a universal joint, which universal joint comprises a first wrist joint, a second wrist joint and a first elbow joint wherein: each wrist joint comprises a first part, a second part and a slipring, which slipring comprises a rotor coupled to the first part and a stator coupled to the second part, which rotor is coaxially engageable with the stator and infinitely rotatable relative to the stator such that: the first part of the first wrist joint is infinitely rotatable relative to the second part of the first wrist joint about a first axis, and the first part of the second wrist joint is infinitely rotatable relative to the second part of the second wrist joint about a second axis; the first elbow joint comprises a first portion and a second portion, which first portion is rotatably engageable with the second portion about a third axis; the first wrist joint is coupled to the first elbow joint; and first elbow joint is coupled to the second wrist joint.

From here on in a wrist joint is defined as a rotational joint which comprises a slipring and allows infinite rotation. Moreover, an elbow joint is defined as a rotational joint which does not comprise a slipring and does not necessarily allow infinite rotation.

By means of the first aspect of the invention a universal joint is provided that facilitates rotation about three axes and therefore has three rotational degrees of freedom. Each of the first wrist joint, second wrist joint and first elbow joint may be configured as a passive joint and the three joints may be configured in combination to exhibit a very low risk of gimbal lock. Accordingly the arm device is provided with the benefits of the universal joint.

The first elbow joint may be configured between the two wrist joints as a hinge joint capable of a range of rotation up to 270° and may further be configured such that the third axis is normal to both the first axis and the second axis.

The combination of the first and second wrist joints with the elbow joint in between them provides the universal joint with three rotational degrees of freedom: pitch, yaw and roll. Further, the combination has a very low risk of gimbal lock because the third axis is normal to both the first and second axes, hence making it impossible for the third axis to align with either the first axis or the second axis and cause gimbal lock.

The first and second axes may align when the sliprings of the first and second wrist joints are coaxial with one another. However, rotation of the first elbow joint inherently changes the alignment of the two wrist joints and their respective axes, thereby allowing gimbal lock to be avoided.

The arm device may form part of a master controller configured to control a slave robot. The master controller may comprise a computer for interpreting data from the arm device and producing commands that are transmitted to the robot.

Each of the wrist and elbow joints may be adapted to provide continuous sensing of the rotational position of the joint and this information may be transmitted through the arm device to the computer of the master controller. The computer may then interpret changes in the rotational position data of each joint and produce corresponding commands to control the position of the robot accordingly.

From here on in the arm device will be described in relation to its application as part of a surgical robotic instrument wherein it forms part of a master controller for controlling a slave robot as set out above. However, the arm device may be used in any suitable application requiring one or more of the features: at least three rotational degrees of freedom, electrical conductivity throughout the device and continuous rotational position sensing.

In embodiments of the invention, the second axis intersects the first axis at an intersection point and the third axis intersects the first axis and the second axis at the intersection point.

In such embodiments of the invention the intersection of the three axes of rotation may mirror the type of rotation achievable with the human wrist which also allows rotation about three intersecting axes. This means that a user of the arm device may manipulate the arm device in a manner that feels more natural and intuitive, especially if the universal joint of such embodiments of the invention is positioned close to the user's wrist when in use.

In embodiments of the invention, the arm device further comprises at least one additional elbow joint; wherein: each additional elbow joint comprises a first portion and a second portion, which first portion is rotatably engageable with the second portion about an additional axis; and each additional elbow joint is coupled to the universal joint.

In such embodiments of the invention each additional elbow joint provides the arm device with an additional degree of freedom. This in turn provides an operator with greater freedom of movement and further reduces the risk of gimbal lock occurring within the arm device.

In embodiments of the invention, the arm device further comprises at least one additional wrist joints; wherein: each additional wrist joint comprises a first part, a second part and a slipring, which slipring comprises a rotor coupled to the first part and a stator coupled to the second part, which rotor is coaxially engageable with the stator and infinitely rotatable relative to the stator such that the first part is infinitely rotatable relative to the second part about an additional axis; and each additional wrist joint is coupled to the universal joint.

In such embodiments of the invention each additional wrist joint provides the arm device with an additional degree of freedom. This in turn provides an operator with greater freedom of movement and further reduces the risk of gimbal lock occurring within the arm device.

In embodiments of the invention, the first part of each wrist joint is rotatably engageable with the second part of the corresponding wrist joint.

In such embodiments of the invention the first and second parts of each wrist joint may be engageable with one another independently to the rotor and stator being engageable with one another. However, in use, rotation of the first part relative to the second part will correspond to rotation of the rotor relative to the stator.

The rotor and stator may be particularly, but not exclusively, adapted to provide electrical conductivity through the corresponding wrist joint while the first and second parts may be particularly, but not exclusively, adapted to provide an engagement with structural integrity. Therefore, the engagement between the first and second parts provides the wrist joint with structural integrity, meaning that the slipring can be specially adapted to perform its primary function, conducting electricity through the joint. Thus each element of the wrist joint may be specially adapted to perform a certain function such that the overall wrist joint has greater strength, durability and functionality.

In embodiments of the invention, each wrist joint further comprises a bearing, which bearing comprises an inner surface and an outer surface, wherein: the inner surface is rotatable relative to the outer surface and engageable with the first part of the wrist joint; and the outer surface is engageable with the second part of the wrist joint such that the first part is rotatably engageable with the second part via the bearing.

In such embodiments of the invention the bearing may be adapted such that the outer surface rotates about the inner surface with low friction exhibited. Rotation of the first part relative to the second part may therefore be performed with a small amount of wear associated with the action. Thus the bearing provides the wrist joint with greater durability.

In embodiments of the invention, the first part of each wrist joint is electrically coupled to the second part of that wrist joint via the slipring.

In such embodiments of the invention the electrical conductivity of the slipring (from the rotor to the stator and vice versa) allows control information to be transmitted from the first part to the second part, or vice versa, even though the wrist joint facilitates infinite rotation.

Each elbow joint may facilitate finite rotation only and therefore the first portion may be electrically coupled to the second portion by any suitable means, such as via an electrical conductor or wire.

In embodiments of the invention, each wrist joint further comprises a first electrical conductor coupled to the rotor and a second electrical conductor coupled to the stator such that the first electrical conductor is electrically coupled to the second electrical conductor via the slipring.

In such embodiments of the invention the electrical conductors may be coupled to electrical conductors of adjacent joints so that the arm device may be provided with electrical conductivity from a first end to a second end via the joints. Accordingly, control information may be transmitted from the first end to the second end through a physical and reliable electrical connection, thus ensuring that an operator's commands are reliably transmitted to the computer of the master controller so that they may, in turn be transmitted to the slave robot to be carried out.

In embodiments of the invention, each wrist joint further comprises a wrist joint sensor configured to measure an angle of rotation of the respective wrist joint.

In such embodiments of the invention each wrist joint sensor may be any suitable non-contact angle measurement sensor such as an optical sensor or a magnetic sensor, for example. As a non-contact sensor, each wrist joint sensor may measure the angle of rotation the respective wrist joint despite infinite rotation being possible.

In embodiments of the invention, each wrist joint sensor comprises a magnet coupled to the rotor of the respective wrist joint and a magnetism sensor fixed relative to the stator of the respective wrist joint and adapted to detect the magnet.

In such embodiments of the invention the magnetism sensor may sense the angular position of the associated magnet. This information may be correlated to the corresponding angular position of rotor in relation to the stator which in turn defines the angular position of the first part in relation to the second part of the wrist joint.

Therefore, the information sensed by the magnetism sensor may be transmitted through the arm device, via electrical conductors for example, to the computer of the master controller which interprets the sensed information and provides corresponding positional commands to a slave robot which it can carry out through actuation.

In embodiments of the invention, each magnet is coupled to a distal end of the corresponding rotor and the first electrical conductor is coupled to a proximal end of the rotor.

In such embodiments of the invention, the proximal end of the rotor may be positioned towards the first part and the distal end of the rotor may be positioned towards the second part. The magnetism sensor is fixed relative to the stator and may be coupled to the second part. Hence the magnet coupled to the distal end of the rotor may be in close proximity to the magnetism sensor to allow accurate and reliable detection of the magnet by the magnetism sensor.

In embodiments of the invention, the or each elbow joint further comprises an elbow joint sensor configured to measure an angle of rotation of the respective elbow joint.

In such embodiments of the invention the or each elbow joint sensor may be any suitable non-contact angle measurement sensor such as an optical sensor or a magnetic sensor, for example.

In embodiments of the invention, the or each elbow joint sensor comprises a magnet fixed relative to the first portion of the respective elbow joint and a magnetism sensor fixed relative to the second portion of the respective elbow joint and adapted to detect the magnet.

In such embodiments of the invention the magnetism sensor may sense the angular position of the associated magnet. This information may be correlated to the corresponding angular position of the first portion in relation to the second portion of the elbow joint.

Therefore, similarly to magnetism sensors located in the wrist joints, the information sensed by each elbow joint magnetism sensor may be transmitted through the arm device, via electrical conductors for example, to the computer of the master controller which interprets the sensed information and provides corresponding positional commands to a slave robot which it can carry out through actuation.

In embodiments of the invention, at least one magnet is diametrically magnetised.

A diametrically magnetised magnet is a circular magnet that comprises a north pole and a south pole positioned diametrically opposite to one another. Therefore, as the magnet rotates about its axis, so will the vector between the north and south poles and the associated magnetic field. The magnetism sensor may therefore detect variations in magnetic flux caused by the magnet's rotation and associate this variation with a change in angular position.

In a wrist joint, a diametrically magnetised magnet may be coaxially coupled to the rotor so that it rotates about its axis relative to the magnetism sensor when the rotor rotates about its axis relative to the stator.

In some embodiments of the invention, elbow joints may be configured as hinge joints, for example, wherein the second portion comprises a socket and the first portion comprises a shaft rotatably engageable with the socket. In such elbow joints a diametrically magnetised magnet may be coaxially coupled to the shaft of the first portion so that it rotates about its axis relative to the magnetism sensor coupled to the second portion when the shaft rotates about its axis relative to the socket.

In other embodiments of the invention, elbow joints may be configured as any suitable form of joint that facilitates a finite range of rotation between the first portion and the second portion.

In embodiments of the invention, at least one magnetism sensor comprises one of a magnetometer of Hall effect sensor.

A magnetometer is a device that measures magnetism and is capable of measuring at least one of the direction, strength or relative change of a magnetic field at a particular location. Therefore the magnetometer allows the magnetism sensor to measure the direction and/or relative change of the magnetic field emitted from the sensor and accordingly calculate the angular position of the magnet as set out above.

A Hall effect sensor is a type of magnetometer that measures a voltage induced by varying magnetic flux which may be caused as the magnet and its associated polarity rotates relative to the Hall effect sensor. Therefore the Hall effect sensor allows the magnetism sensor to measure the relative angular position of the magnet as an induced voltage which may be interpreted by the magnetism sensor so that corresponding commands can be sent to the robot via the computer of the master controller.

In embodiments of the invention, the arm device comprises a static end portion located at a proximal end of the arm device and a moveable end portion located at a distal end of the arm device, wherein the moveable end portion is electrically coupled to the static end portion via the joint or joints.

In such embodiments the static end portion may be mounted to a main body of the master controller. The moveable end portion may comprise a handle to be held by an operator of the master controller and may therefore be moved by the operator in order to control the robot.

The moveable end portion may further comprise control input features, such as buttons, triggers or switches, which may be operated by the operator to command specific actions of the robot. Such commands may be transmitted via electrical conductors from the moveable end portion to the static end portion and the associated master controller.

In embodiments of the invention, the moveable end portion comprises a motion sensor.

In such embodiments the motion sensor is able to detect when movement of the moveable end portion occurs and this information may be transmitted, via electrical conductors for example, to the static end portion and associated master controller. The motion sensor data may be used for a wide range of purposes such as switching the system between 'standby' and 'awake' modes. When the motion sensor fails to detect movement of the moveable end portion for a period of time the master controller may interpret this data as inactivity and switch the system into an energy-saving 'standby' mode. When the motion sensor detects movement of the moveable end portion while the system is in 'standby' mode, the master controller may receive this information and switch the system into a fully-functioning 'awake' mode.

In embodiments of the invention, the motion sensor comprises an accelerometer.

In such embodiments the accelerometer is able to detect the acceleration experienced by the moveable end portion and this information may be transmitted, via electrical conductors for example, to the static end portion and associated master controller. This may be particularly useful in detecting whether the moveable end portion has been dropped by the operator of the arm device. The master controller may be adapted to detect when the acceleration sensed by the accelerometer corresponds with acceleration due to gravity meaning that the moveable end portion has likely been dropped. In such circumstances the master controller may override or cancel any positional commands registered by the magnetism sensors in the joints, for example, and instead instruct the robot to hold the position it had before the 'drop' measurement was recorded.

This may be particularly useful if the arm device and master controller is being used to control a surgical robot where an unintended movement of the robot could cause harm to the patient that the robot is being used to operate on. Rather than the robot mimicking the commands associated with the moveable end portion being dropped, the robot would hold its position until the moveable hand portion is reacquired by the operator and a button is pressed, for example, to confirm that the operator is ready to provide further commands for the robot.

The accelerometer is also used to regularly check the accuracy of the joint sensing provided by the magnet and magnetism sensor (for example every 0.05 seconds). This accuracy check ensures that movements performed by the user of the master controller are mirrored by the robot being controlled. The added layer of safety redundancy is particularly advantageous in surgical applications where inaccuracy in a robot's movements can have serious consequences.

Accelerometers also have the tendency to drift over time (typically within a scale of 10 to 30 seconds). In order to prevent accelerometer drift and prevent the drift from affecting the accuracy check set out above, positional information from the magnet-based joint sensors is relayed to the accelerometer over intervals of time that are substantially shorter than the time required for drift to occur, such as every 2 seconds.

According to a second aspect of the invention, there is provided a surgical device comprising a robot and a master controller configured to control the robot, which master controller comprises a base and an arm device according to the first aspect of the invention, wherein the arm device extends from the base.

By means of the present invention an operator of the surgical device, such as a surgeon, may use the master controller to control the robot. The master controller may be provided with an arm device comprising a universal joint and may therefore allow the operator to carry out complex spatial actions, requiring at least three degrees of freedom, while using the arm device to feed instructions to the master controller.

Each of the wrist and elbow joints may be adapted to provide continuous sensing of the rotational position of the joint and this information may be transmitted through the arm device to the master controller.

The master controller may comprise a computer for interpreting changes in the rotational position data of each joint and produce corresponding commands to control the position of the robot accordingly.

In embodiments of the invention the master controller further comprises a view port.

In such embodiments the master controller may be mounted on a platform, such as a desk or table, at a height suitable to allow an operator of the master controller to operate the arm devices and simultaneously look into the view port order to control the robot, for example during a surgical procedure. The view port may be configured to show video footage to aid the operator in controlling the robot. The video footage may be recorded by the slave robot itself or it may be recorded by an auxiliary instrument, such as an endoscope during a surgical procedure. The video footage may be transmitted to the master controller so that it may be displayed in the view port to provide a real-time view of the robot or from the robot's perspective.

According to a third aspect of the invention, there is provided a wrist joint comprising a first part, a second part, a magnet, a magnetism sensor and a slipring, which slipring comprises a rotor coupled to the first part and a stator coupled to the second part, which rotor is coaxially engageable with the stator and infinitely rotatable relative to the stator, wherein: the magnet is coupled to the rotor; and the magnetism sensor is fixed relative to the stator and is adapted to detect the magnet.

The wrist joint may form part of an arm device according to the first aspect of the invention and more specifically it may form part of a universal joint according to the first aspect of the invention.

The first and second parts of each wrist joint may be engageable with one another independently to the rotor and stator being engageable with one another. However, in use, rotation of the first part relative to the second part will correspond to rotation of the rotor relative to the stator.

The rotor and stator may be particularly, but not exclusively, adapted to provide electrical conductivity through the corresponding wrist joint while the first and second parts may be particularly, but not exclusively, adapted to provide an engagement with structural integrity. Therefore, the engagement between the first and second parts provides the wrist joint with structural integrity, meaning that the slipring can be specially adapted to perform its primary function, conducting electricity through the joint. Thus each element of the wrist joint may be specially adapted to perform a certain function such that the overall wrist joint has greater strength, durability and functionality.

The wrist joint may further comprise a bearing, which bearing comprises an inner surface and an outer surface, wherein: the inner surface is rotatable relative to the outer surface and engageable with the first part of the wrist joint; and the outer surface is engageable with the second part of the wrist joint such that the first part is rotatably engageable with the second part via the bearing. The bearing may be adapted such that the outer surface rotates about the inner surface with low friction exhibited. Rotation of the first part relative to the second part may therefore be performed with a small amount of wear associated with the action. Thus the bearing provides the wrist joint with greater durability.

The first part of the wrist joint may be electrically coupled to the second part of the wrist joint via the slipring. The electrical conductivity of the slipring (from the rotor to the stator and vice versa) allows control information to be transmitted from the first part to the second part, or vice versa, even though the wrist joint facilitates infinite rotation.

The wrist joint may further comprise a first electrical conductor coupled to the rotor and a second electrical conductor coupled to the stator such that the first electrical conductor is electrically coupled to the second electrical conductor via the slipring. The electrical conductors may be coupled to electrical conductors of adjacent joints so that the arm device may be provided with electrical conductivity from a first end to a second end via each of the joints it comprises. Accordingly, control information may be transmitted from the first end to the second end through a physical and reliable electrical connection, thus ensuring that an operator's commands are reliably transmitted to the computer of the master controller so that they may, in turn be transmitted to the slave robot to be carried out.

The magnetism sensor may sense the angular position of the associated magnet. This information may be correlated to the corresponding angular position of rotor in relation to the stator which in turn defines the angular position of the first part in relation to the second part of the wrist joint.

The above discussion is not intended to represent every example embodiment or every implementation within the scope of the current or future claim sets. The figures and Detailed Description that follow also exemplify various example embodiments. Various example embodiments may be more completely understood in consideration of the following Detailed Description in connection with the accompanying drawings.

One or more embodiments will now be described by way of example only with reference to the accompanying drawings in which.

Figure 6A:
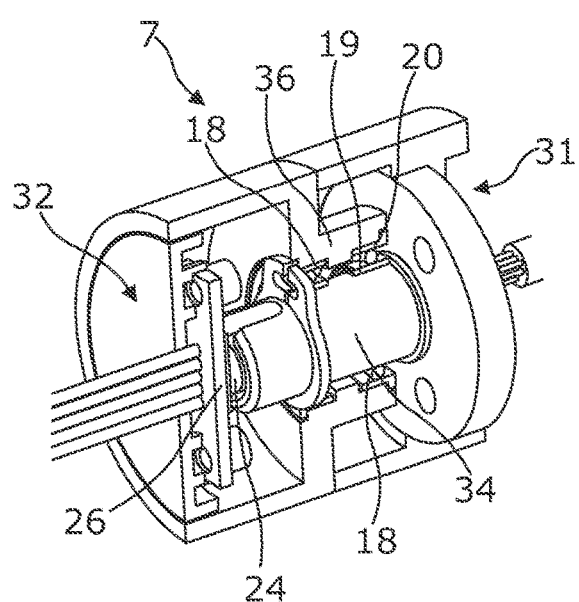
Figure 6B:
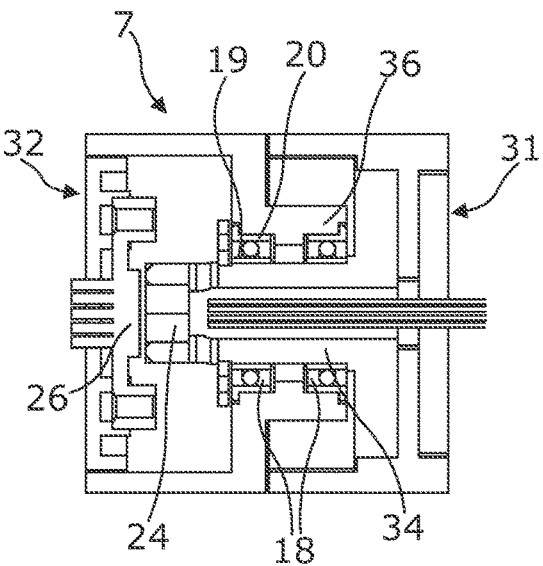

FIGS. 6*a* and 6*b* are close-up, cross-sectional schematic representations of an elbow joint according to an embodiment of the first aspect of the invention.

Figure 7:
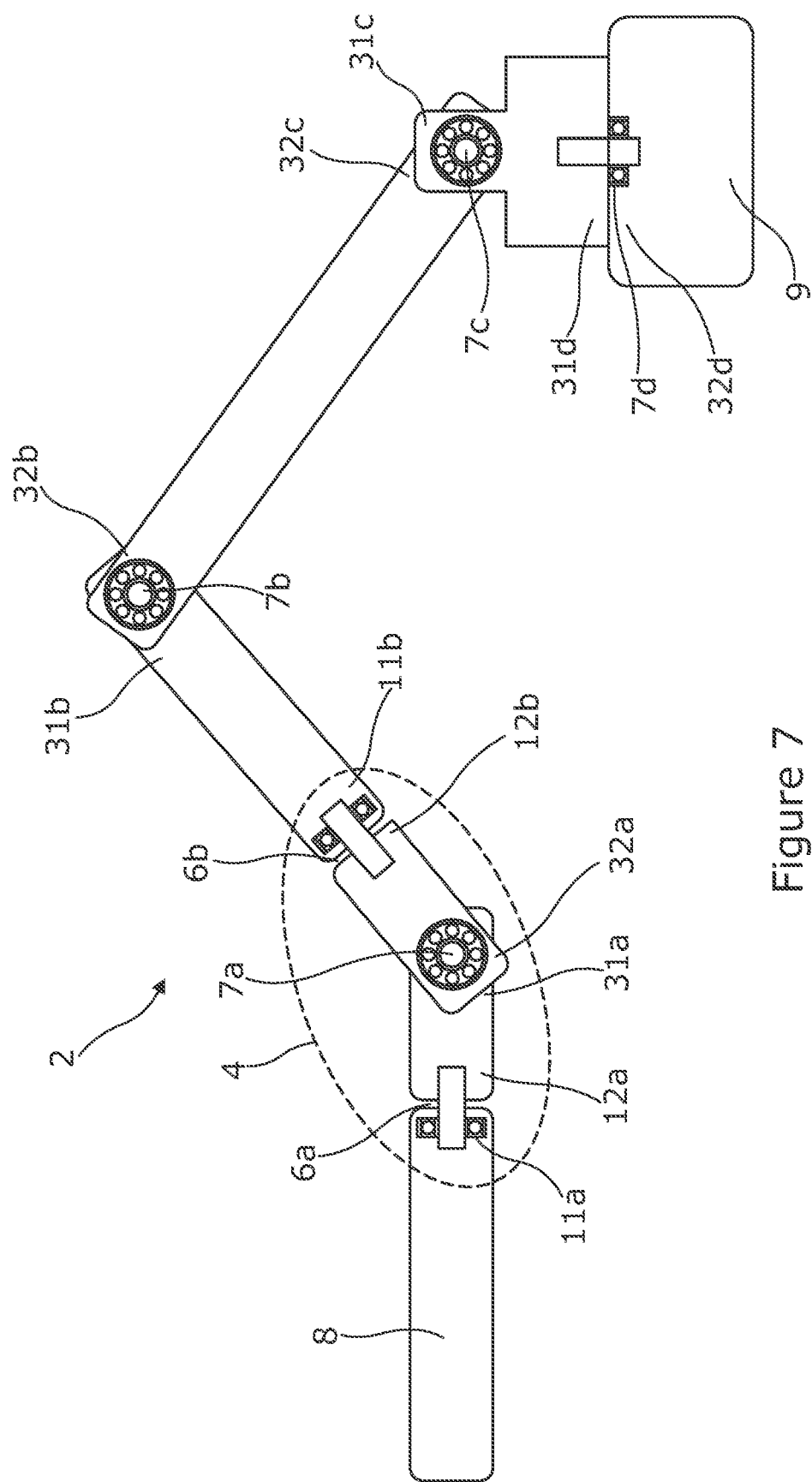

FIG. 7 is a simplified schematic representation of an arm device according to an embodiment of the first aspect of the invention.

Figure 8:
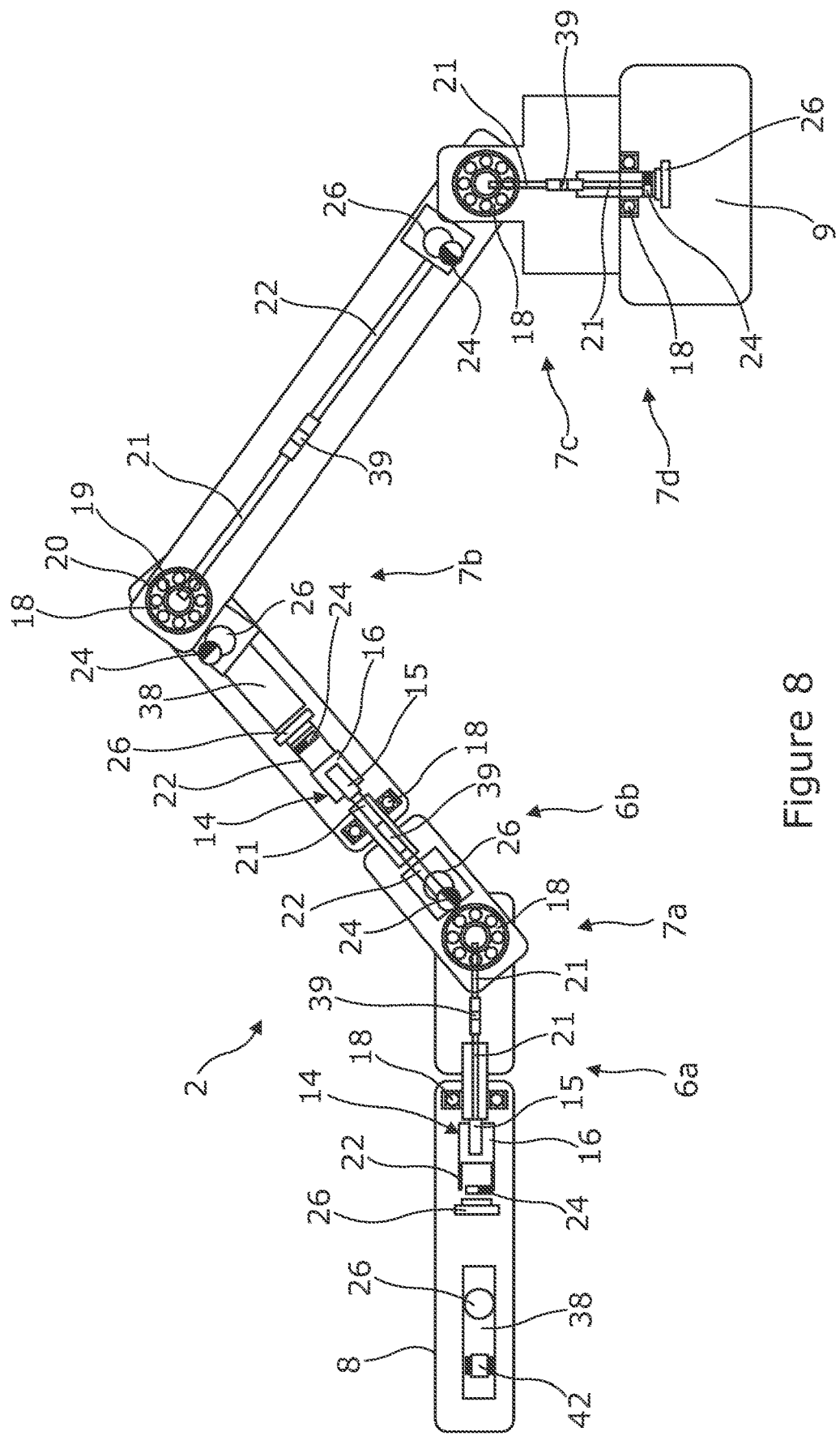

FIG. 8 is a further representation of the arm device shown in FIG. 7 which additionally shows certain internal components.

Figure 9:
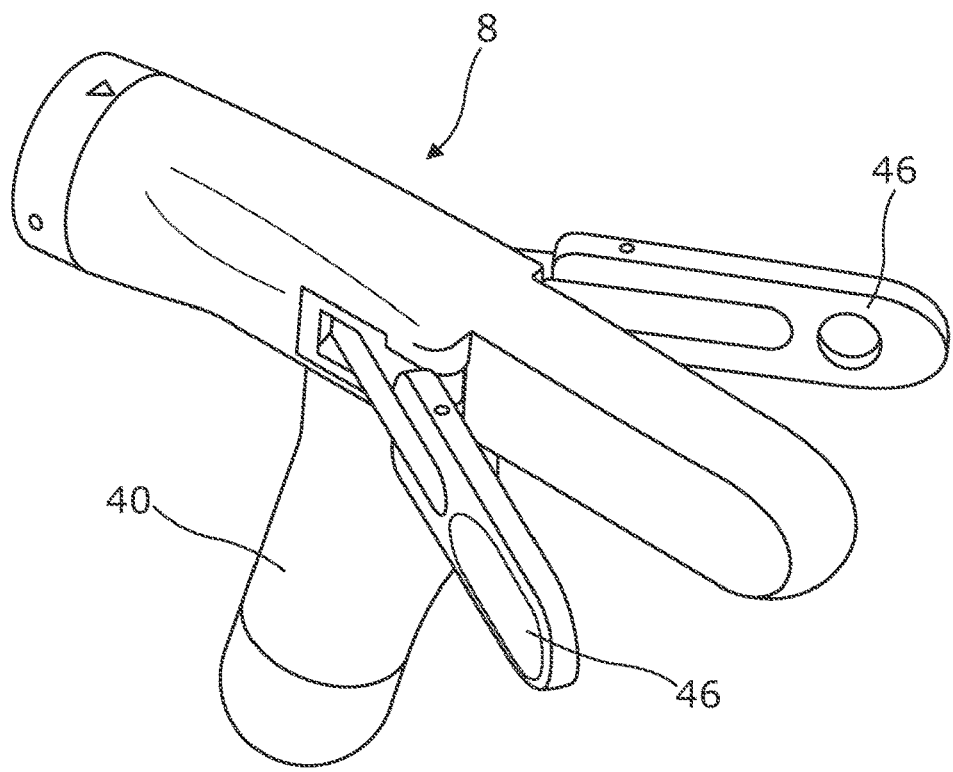

FIG. 9 is a schematic representation of a moveable end portion according to an embodiment of the first aspect of the invention and shows certain internal components.

Figure 10:
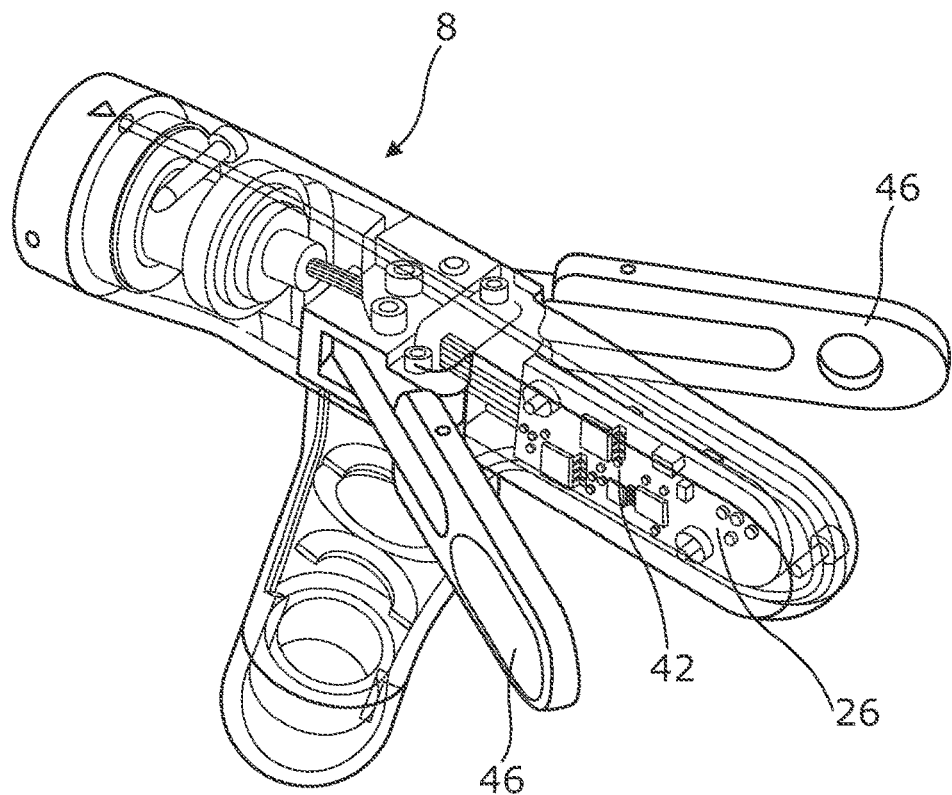

FIG. 10 is a schematic representation the moveable hand portion shown in FIG. 9 with a transparent outer casing.

Figure 11A:
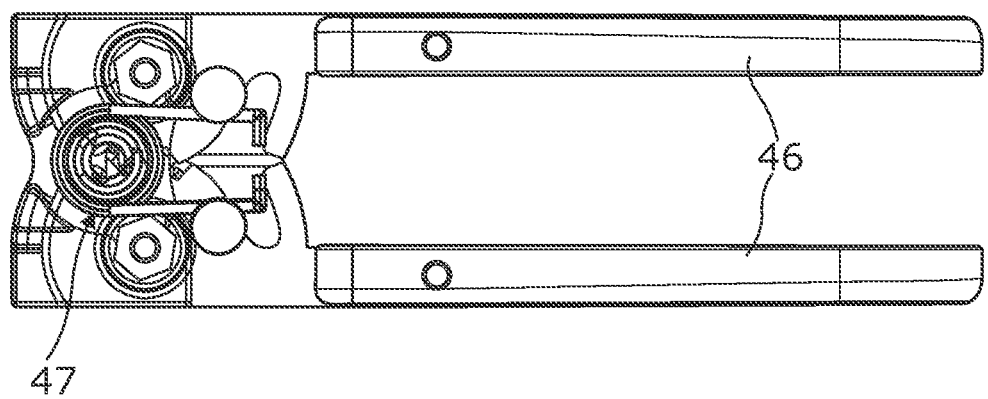
Figure 11B:
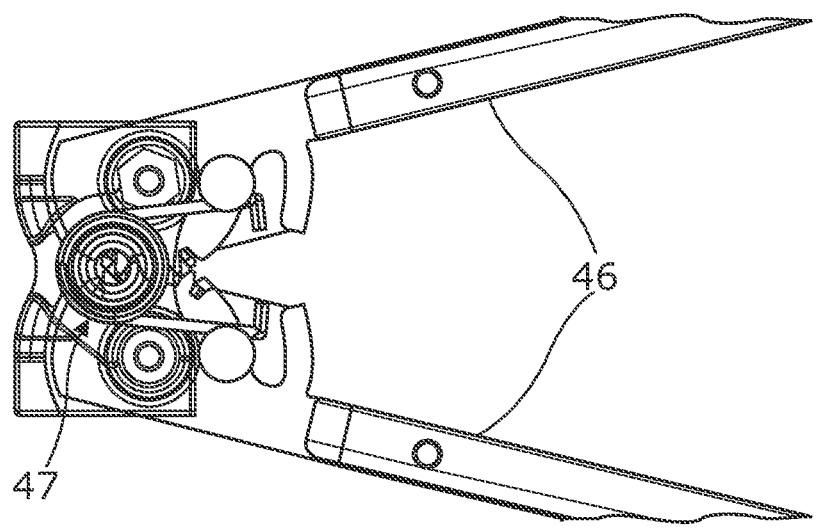
Figure 11C:
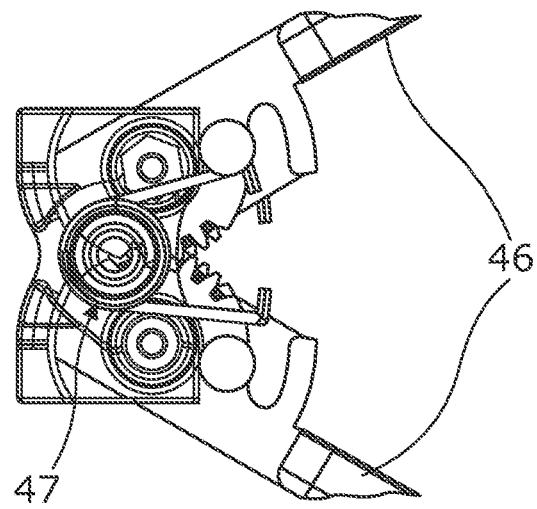

FIGS. 11*a*, 11*b* and 11*c* are schematic representations of internal components that form part of the moveable hand portion shown in FIG. 9.

Figure 12:
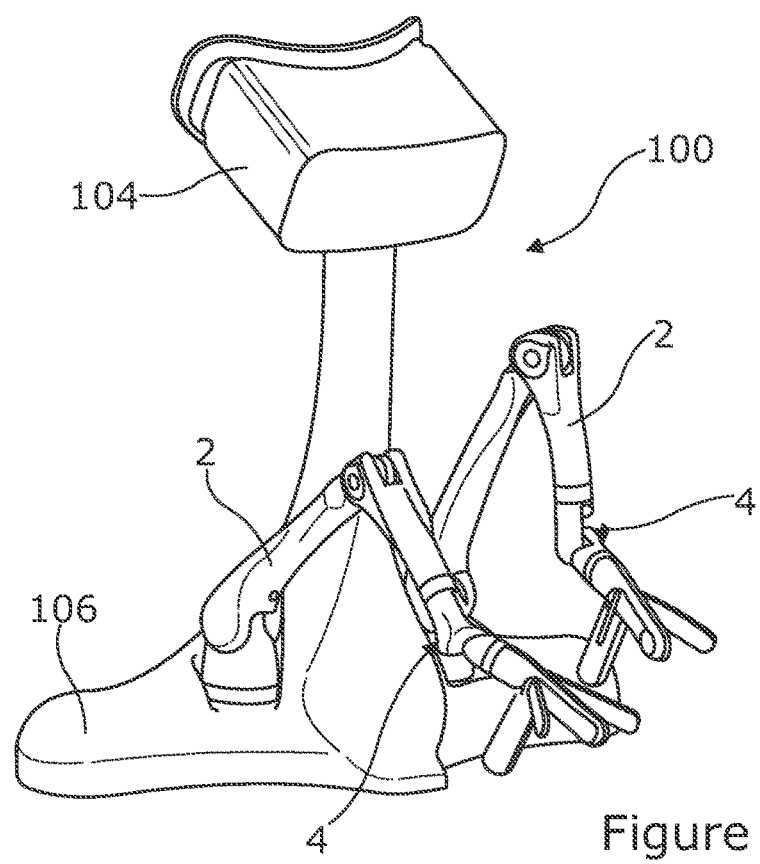

FIG. 12 is a schematic representation of a master controller according to an embodiment of the second aspect of the invention.

Figure 13:
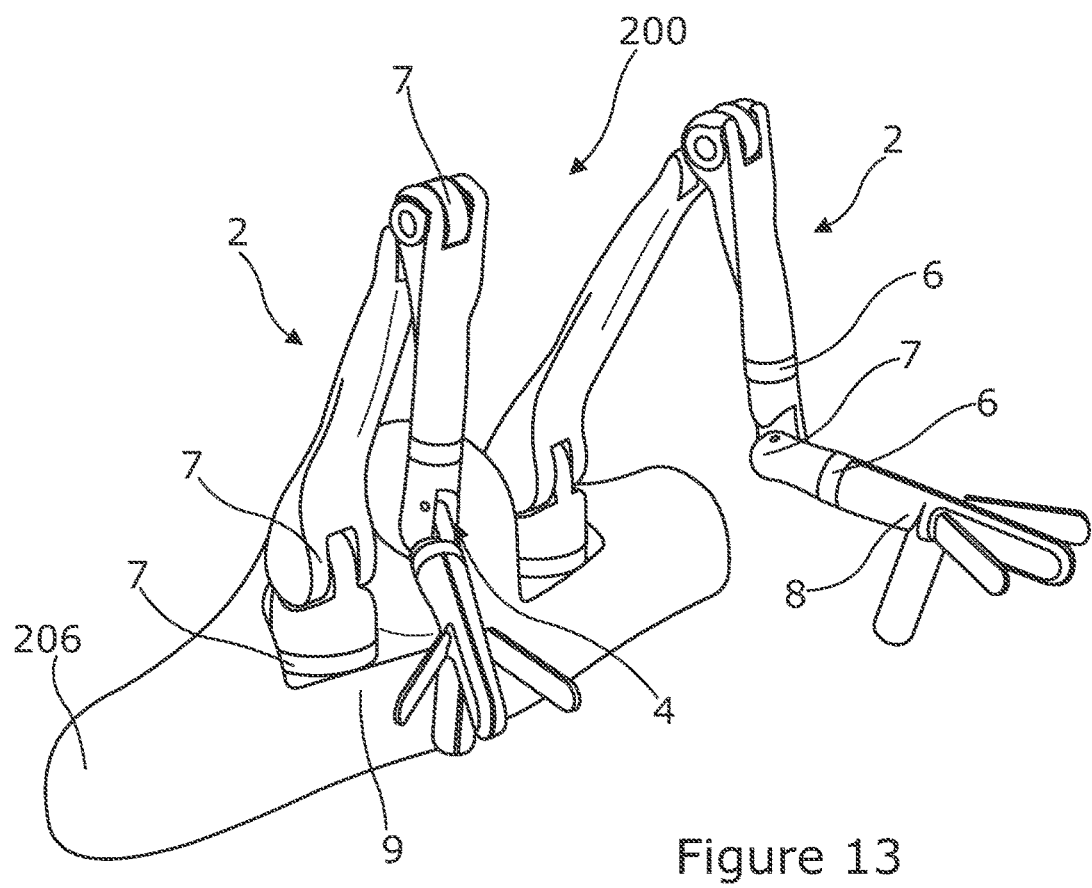

FIG. 13 is a schematic representation of a further master controller according to an embodiment of the second aspect of the invention.

Figure 14:
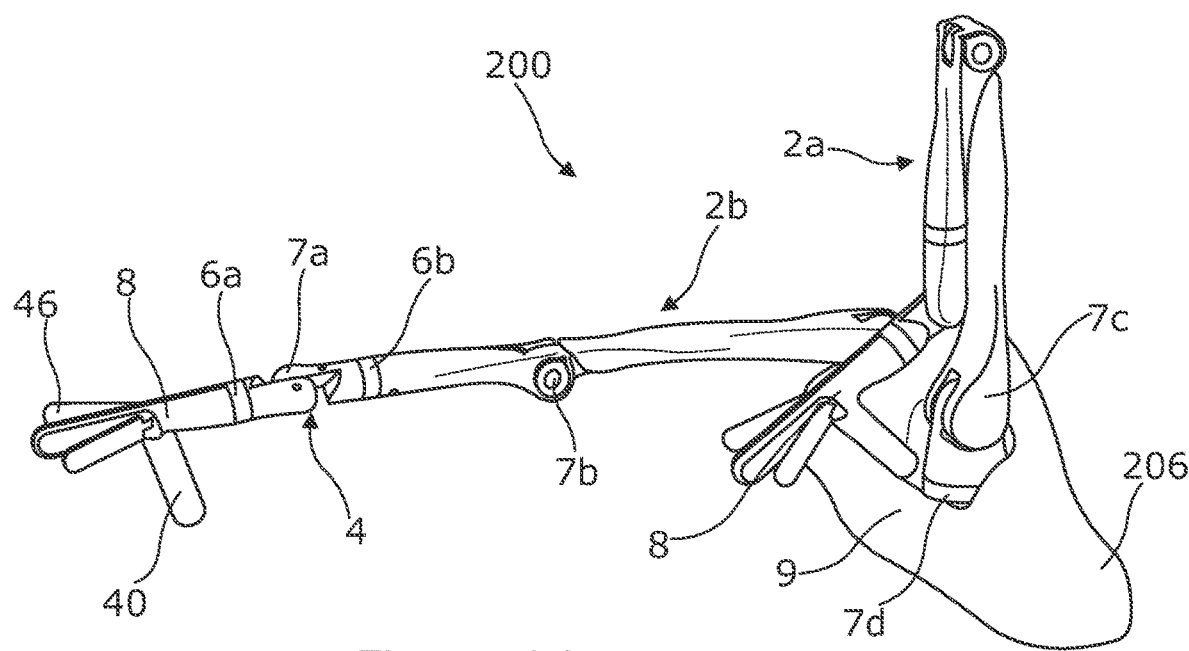

FIG. 14 is a schematic representation of the master controller shown in FIG. 13 with each arm device in a different configuration.

Figure 15:
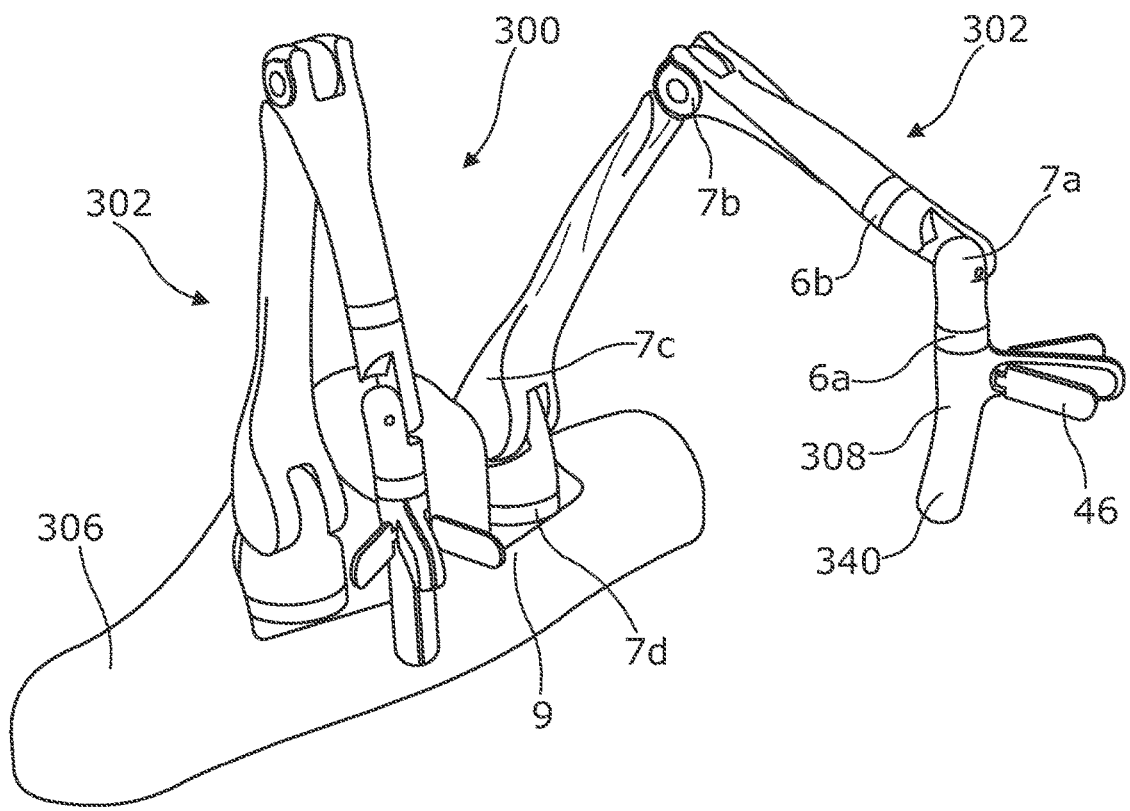

FIG. 15 is a schematic representation of a further master controller according to an embodiment of the second aspect of the invention, where each arm device is configured with a vertical movable end portion.

Figure 16:
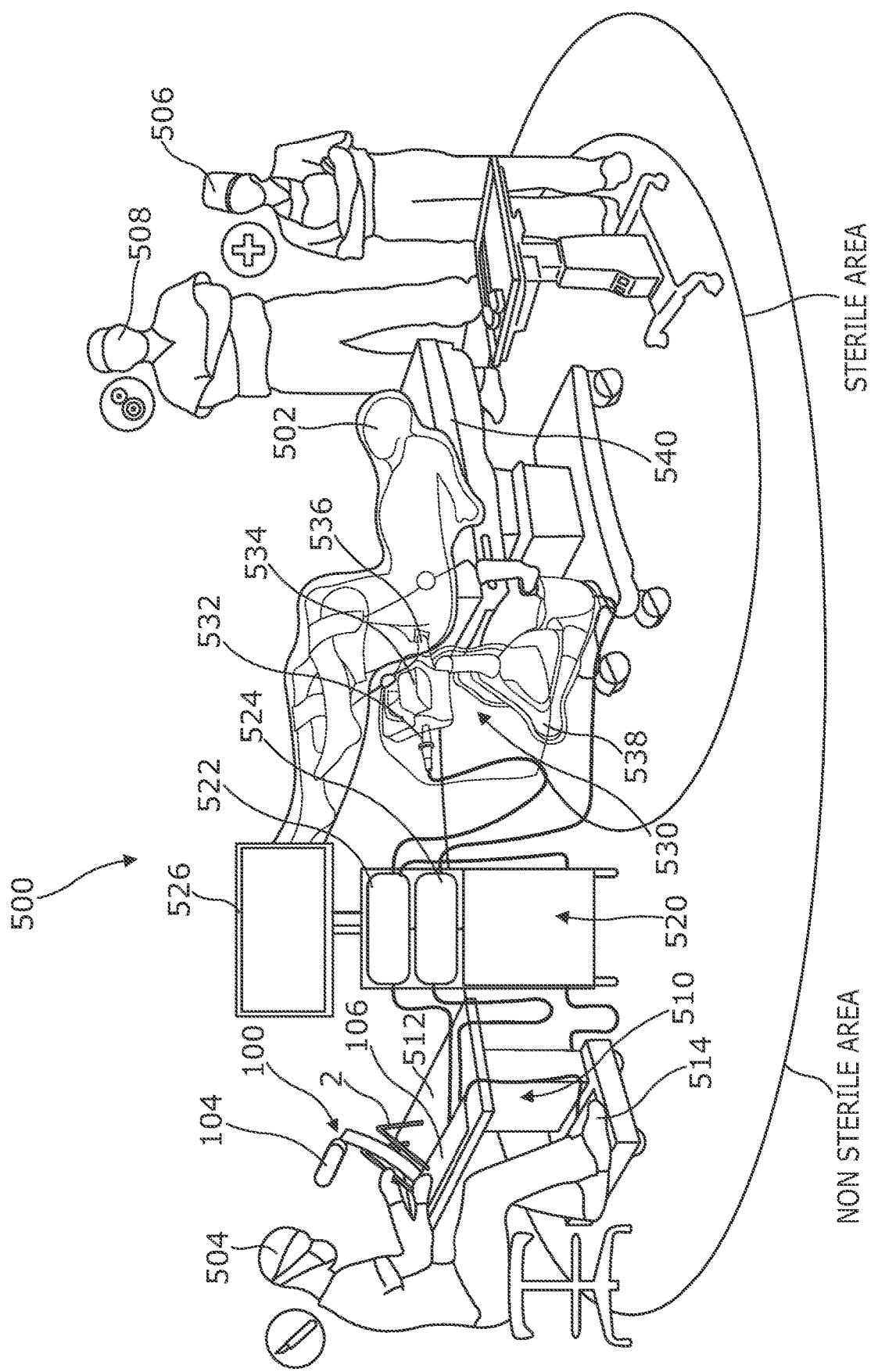

FIG. 16 is a schematic representation of an operating theatre comprising a master controller according to an embodiment of the second aspect of the invention in use.

Figure 1:
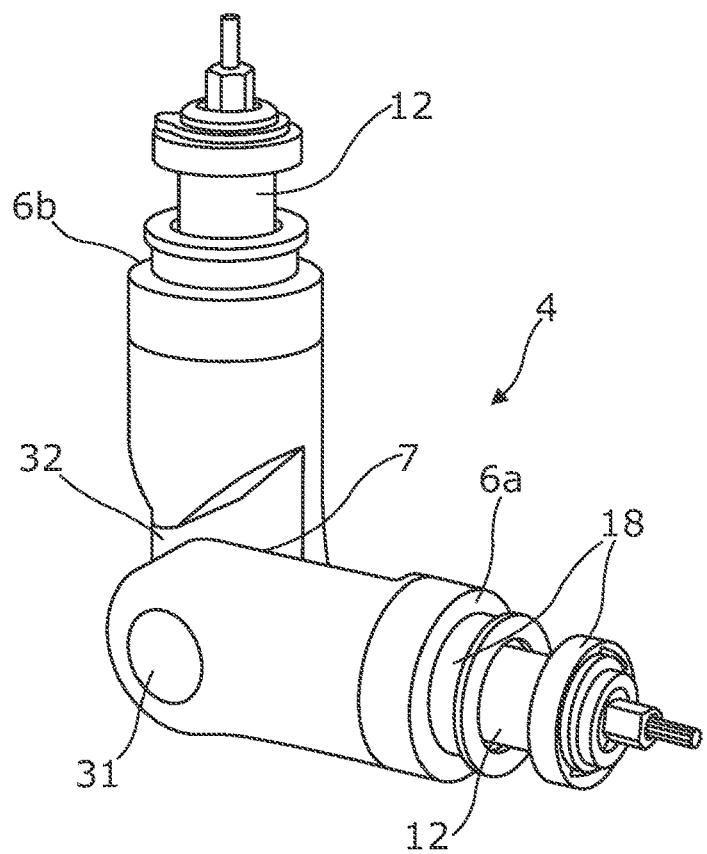
FIG. 1 is a schematic representation of a universal joint according to an embodiment of the first aspect of the invention.

Referring initially to FIG. 1, a universal joint according to the first aspect of the invention is designated generally by the reference numeral 4. The universal joint 4 comprises two wrist joints 6*a*, 6*b* and an elbow joint 7 positioned between the two wrist joints 6. The elbow joint 7 comprises a first portion 31 and a second portion 32. Each wrist joint comprises a first part (not shown), a second part 12 and, in this embodiment, a pair of bearings 18. However, the wrist joints 6 may comprise any suitable number of bearings.

Figure 2:
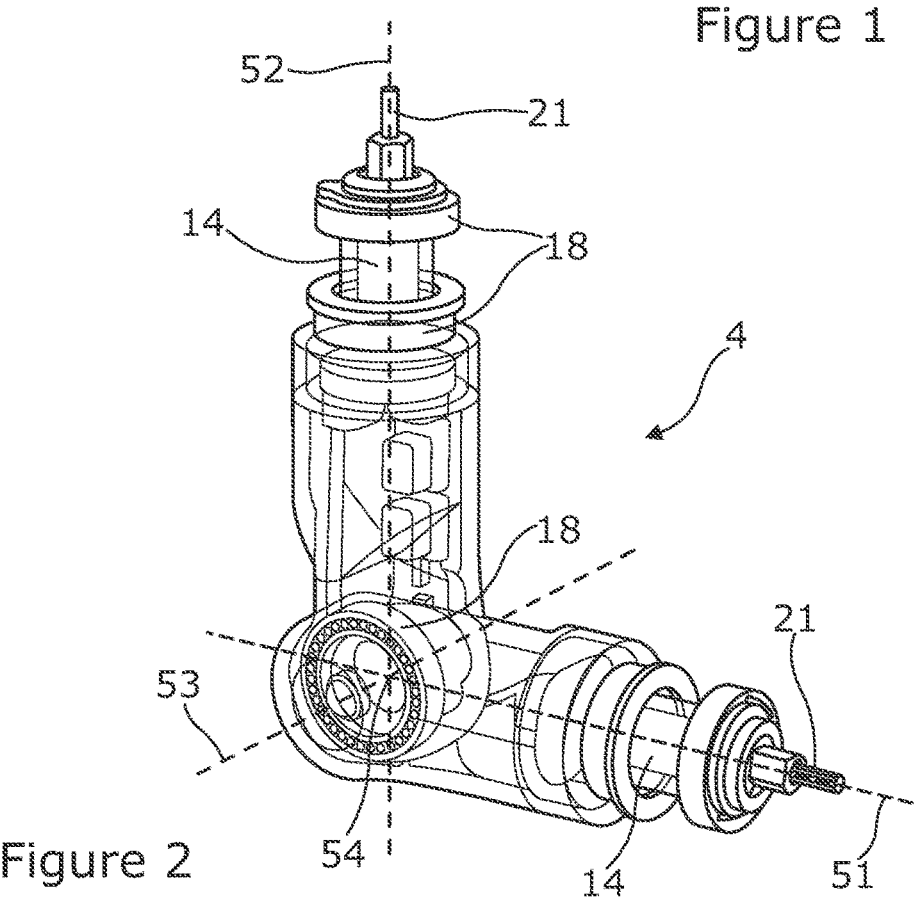
FIG. 2 is a schematic representation of the universal joint shown in FIG. 1 with a transparent outer casing.
Figure 5:
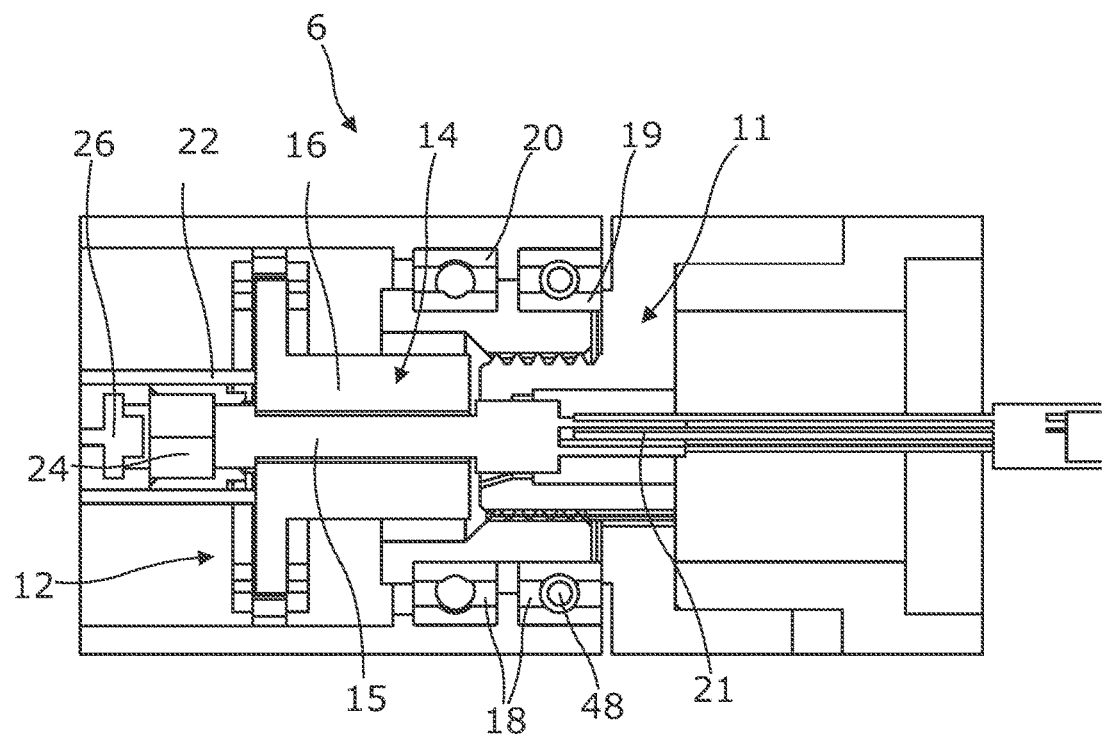
FIG. 5 is a close-up, cross-sectional schematic representation of a wrist joint according to an embodiment of the first and third aspects of the invention.

FIG. 2 shows the same universal joint 4 shown in FIG. 5 with a transparent outer casing to reveal the internal components. Each wrist joint 6 comprises a slip ring 14 and the elbow joint 7 comprises a bearing 18 similar to those comprised in the wrist joints 6. Similarly to the wrist joints 6, the elbow joint 7 may comprise any suitable number of bearings 18.

FIG. 2 additionally shows a first axis 51, a second axis 52 and a third axis 53. The first part of the first wrist joint 6*a* is infinitely rotatable relative to the second part of the first wrist joint 6*a* about the first axis 51, the first part of the second wrist joint 6*b* is infinitely rotatable relative to the second part of the second wrist joint 6*b* about the second axis 52, and the first portion 31 of the elbow joint 7 is rotatable with the second portion 32 about the third axis 53.

In this embodiment of the invention the first, second and third axes 51, 52, 53 intersect one another at an intersection point 54. The universal joint 4 may therefore be manipulated, through rotation of each of its joints, with respect to a common point which mimics the rotation achievable with the human wrist. This may allow a user of an arm device (such as those shown in FIGS. 7, 8 and 12 to 15) to manipulate the arm device in a manner that feels natural and intuitive and may avoid the user feeling the need to hold his or her wrist in an unusual or uncomfortable position to achieve the desired manipulation of the arm device.

Figure 3:
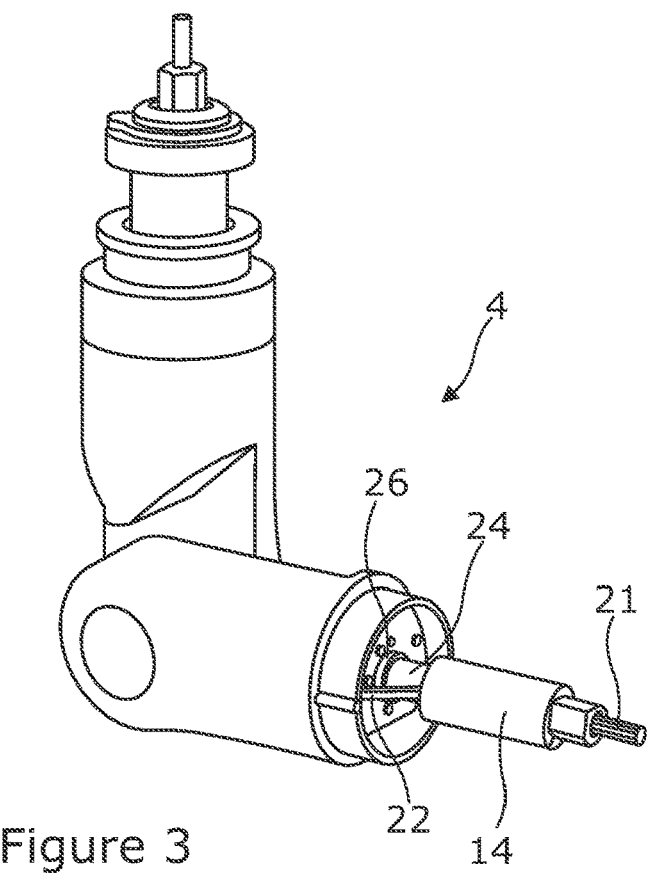
FIG. 3 is a schematic representation of the universal joint shown in FIG. 1 with some components removed to reveal other components.

Referring now to FIG. 3, the universal joint is shown with the bearings 18 and elements of the second part 12 of the wrist joint 6*a* removed to reveal the internal components of said wrist joint 6. The wrist joint 6 comprises a magnet coupled to the slip ring 14 and a magnetism sensor 6 coupled to the second part 12 and adapted to detect the magnet 24. The wrist joint also comprises first and second electrical conductors 21, 22 coupled to the slip ring 14.

Figure 4:
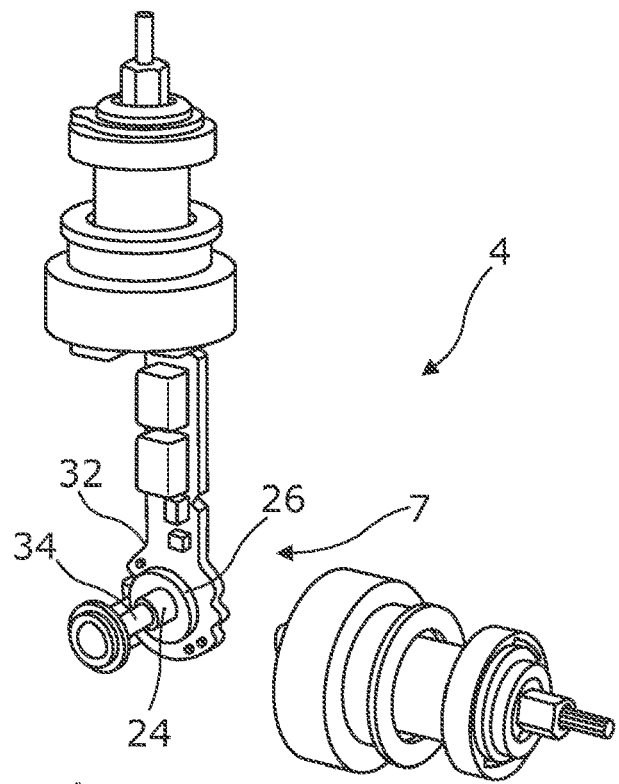
FIG. 4 is a schematic representation of the universal joint shown in FIG. 1 with different components removed to reveal other components.

Referring now to FIG. 4, the universal joint 4 is shown with the outer casing and the bearing 18 of the elbow joint 7 removed in order to reveal internal components of said elbow joint 7. The elbow joint 7 comprises a shaft 34 coupled to the first portion (not shown) and a magnet 24 coupled to the shaft 34. The elbow joint 7 further comprises a magnetism sensor 26 coupled to the second portion 32 (partially shown), which magnetism sensor 26 is adapted to detect the magnet.

Referring now to FIG. 5, a cross-sectional view of a wrist joint 6 according to an embodiment of the first and/or third aspects of the invention is shown which is equivalent to the wrist joints 6*a*, 6*b* shown in FIGS. 1 to 4. The slip ring 14 comprises a rotor 15 coupled to the first part 11 of the wrist joint 6 and a stator 16 coupled to the second part 12. The rotor 15 is coaxially engageable with the stator 16 and infinitely rotatable relative to the stator 16.

The magnet 24 is coupled to the rotor 15. The magnetism sensor 26 is coupled to the second part 12 which is in turn coupled to the stator 16 such that the magnetism sensor 26 is fixed relative to the stator 16. Therefore, as the rotor 15 rotates relative to the stator 16, the magnet 24 simultaneously rotates relative to the magnetism sensor 26.

In this embodiment the magnet 24 is a diametrically magnetised magnet and the magnetism sensor 26 comprises a Hall effect sensor. The magnet 24 is coaxially coupled to the rotor 15 so that the vector between the magnet's north and south poles rotates about the magnet's axis relative to the magnetism sensor 26 when the rotor 15 rotates about its axis relative to the stator 16.

Therefore, as the magnet 24 rotates about its axis, so will the associated magnetic field such that the magnetism sensor 26 may detect variations in magnetic flux caused by the magnet's rotation and associate this variation with a change in the angular position of the magnet 24 and the associated rotor 15. Hence the magnetism sensor 26 may detect the angular position of the first part 11 of the wrist joint 6 relative to the second part 12.

The Hall effect sensor allows the magnetism sensor 26 to measure the relative angular position of the magnet 24 as an induced voltage which may then be interpreted by the magnetism sensor 26 as changes in angular position of the first part 11 relative to the second part 12. Commands may then be sent to the robot via the computer of the master controller (100, 200) which correspond to the changes in the angular position of the arm device 2 and particularly the wrist joint 6.

The bearings 18 comprise an inner surface 19 engageable with the first part 11 of the wrist joint 6 and an outer surface 20 engageable with the second part 12 of the wrist joint 6. The inner surface 19 is rotatable relative to the outer surface 20 such that the first part 11 is rotatably engageable with the second 12 part via the bearing 18.

In this embodiment the bearings 18 further comprise ball bearings 48 between the inner surface 19 and the outer surface 20 to allow the outer surface 20 to rotate about the inner surface 19 with a low amount of friction. However the bearings 18 may be adapted to provide low friction between the inner surface 19 and the outer surface 20 by any suitable means.

Rotation of the first part 11 relative to the second part 12 may therefore be performed with a low amount of wear associated with the action. Thus the bearings 18 provide the wrist joint 6 with greater durability.

The rotor 15 and stator 16 are each electrically conductive and are adapted such that the rotor 15 is infinitely rotatable within the stator 16 while maintaining electrical connectivity. The first part 11 is thereby electrically coupled to the second part 12 joint via the slipring 14.

Further, the first electrical conductor 21 is coupled to the rotor 15 and the second electrical conductor 22 is coupled to the stator 16 such that the first electrical conductor 21 is electrically coupled to the second electrical conductor 22 via the slipring 14.

The electrical conductors 21, 22 may be coupled to electrical conductors of adjacent joints as shown in FIG. 8.

Referring now to FIGS. 6a and 6b, a cross-sectional view of an elbow joint 7 is shown which is similar to the elbow joints 7 shown in FIGS. 1 to 4. However, this embodiment of the elbow joint 7 comprises two bearings 18 rather than the one provided in the embodiment shown in FIGS. 1 to 4.

The second portion 32 comprises a socket 36 and the first portion 31 comprises a shaft 34 rotatably engageable with the socket 36. The magnet 24, which is diametrically magnetised in this embodiment, is coaxially coupled to the shaft 34 of the first portion 31 and the magnetism sensor 26, which comprises a Hall effect sensor in this embodiment, is coupled to the second portion 36. Therefore, when the shaft 34 rotates about its axis relative to the socket 36, the magnet 24 rotates accordingly relative to the magnetism sensor 26.

The Hall effect sensor allows the magnetism sensor 26 to measure the relative angular position of the magnet 24 as an induced voltage which may then be interpreted by the magnetism sensor 26 as changes in angular position of the first portion 31 relative to the second portion 32. Commands may then be sent to the robot via the computer of the master controller (100, 200) which correspond to the changes in the angular position of the arm device 2 and particularly the elbow joint 7.

In the embodiments of the invention shown in FIGS. 1 to 6b magnetic sensors, each comprising a magnet 24 and magnetism sensor 26, are used as wrist and elbow joint sensors. However, any suitable non-contact angle measurement sensor may be used as a wrist or elbow joint sensor. For example, an optical sensor may be used rather than a magnetic sensor.

Similarly to the bearings 18 shown in FIG. 5, the bearings 18 of the elbow joint 7 comprise an inner surface 19 engageable with the shaft 34 and an outer surface 20 engageable with the socket 36. The inner surface 19 is rotatable relative to the outer surface 20 such that the shaft 34 is rotatably engageable with the socket 36 via the bearings 18.

The bearings 18 further comprise ball bearings 48 between the inner surface 19 and the outer surface 20 to allow the outer surface 20 to rotate about the inner surface 19 with a low amount of friction. However the bearings 18 may be adapted to provide low friction between the inner surface 19 and the outer surface 20 by any suitable means.

Rotation of the shaft 34 relative to the socket 36 may therefore be performed with a low amount of wear associated with the action. Thus the bearings 18 provide the elbow joint 7 with greater durability.

Referring now FIG. 7, an arm device according to the first aspect of the invention is designated generally by the reference numeral 2.

The arm device 2 comprises a universal joint 4, which universal joint 4 is equivalent to the universal joint 4 shown in FIGS. 1 to 4 and comprises a first wrist joint 6a, a second wrist joint 6b and a first elbow joint 7a. The first wrist joint 6a comprises a first part 11a and a second part 12a, which first part 11a is engageable and infinitely rotatable relative to the second part 12a about a first axis. Similarly, the second wrist joint 6b comprises a first part 11b and a second part 12b, which first part 11b is engageable and infinitely rotatable relative to the second part 12b about a second axis. The first elbow joint 7a comprises a first portion 31a and a second portion 32a, which first portion 31a is rotatably engageable with the second portion 32a about a third axis that is normal to both the first axis and the second axis. The first wrist joint 6a is coupled to the first elbow joint 7a which is in turn coupled to the second wrist joint 6b, thus forming the universal joint 4 which has three rotational degrees of freedom—one rotational degree of freedom about each of the first, second and third axes.

The arm device 2 further comprises a plurality of additional elbow joints: a second elbow joint 7b, a third elbow joint 7c and a fourth elbow joint 7d. Each additional elbow joint 7b, 7c, 7d comprises a first portion 31b, 31c, 31d (respectively) and a second portion 32b, 32c, 32d (respectively). Each first portion 31b, 31c, 31d is rotatably engageable with its corresponding second portion 32b, 32c, 32d about an additional axis.

The second elbow joint 7b is directly coupled to the universal joint 4. The third elbow joint 7c is directly coupled to the second elbow joint 7b and is thereby coupled to the universal joint 4. Similarly the fourth elbow joint 7d is directly coupled to the third elbow joint 7c and is thereby coupled to the universal joint 4.

The arm device 2 further comprises a static end portion 9 located at a proximal end of the arm device and a moveable end portion located 8 at a distal end of the arm device, wherein the moveable end portion 8 is coupled to the static end portion 9 via the universal joint 4 and the additional elbow joints 7b, 7c, 7d.

Referring now to FIG. 8, the arm device 2 shown in FIG. 7 is shown with further detail relating to the internal features of the arm device 2.

In accordance with FIG. 7, the arm device 2 comprises: a moveable end portion 8, a first wrist joint 6a, a first elbow joint 7a, a second wrist joint 6b, a second elbow joint 7b, a third elbow joint 7c, a fourth elbow joint 7d and a static end portion 9, each coupled to one another in that order. However, an arm device according to the first aspect of the invention may comprise any suitable combination of joints in any suitable order.

The moveable end portion 8 comprises a printed circuit board (PCB) 38, a motion sensor 42 and a magnetism sensor 26. The motion sensor 42 and the magnetism sensor 26 are both electrically mounted to the PCB 38. The motion sensor 42 and the magnetism sensor 26 may be electrically mounted to the PCB 38 by any suitable means such as soldering.

The magnetism sensor 26 is able to sense the position of a magnet (not shown) coupled to a lever (not shown) that may be actuated relative to the moveable end portion 8. The function of the magnetism sensor 26 is described in further detail in relation to FIGS. 9 and 10.

The motion sensor 42 is able to detect when movement of the moveable end portion 8 occurs and this information may be transmitted, via the PCB 26 and further electrical conductors comprised within the arm device 2, to the static end portion 9 and an associated master controller (such as the master controllers shown in FIGS. 11 to 14).

In this embodiment the motion sensor 42 comprises an accelerometer. The accelerometer is able to detect the acceleration experienced by the moveable end portion 8. This may be particularly useful in detecting whether the moveable end portion 8 has been dropped by the operator of the arm device 2. The master controller may be adapted to detect when the acceleration sensed by the accelerometer corresponds with acceleration due to gravity meaning that the moveable end portion 8 has likely been dropped. In such circumstances the master controller may override or cancel any positional commands registered by the magnetism sensors 26 in the joints 6a, 7a, 6b, 7b, 7c, 7d and instead instruct the robot to hold the position it had before the 'drop' measurement was recorded.

This may be particularly useful if the master controller, and particularly the arm device 2, is being used to control a surgical robot where an unintended movement of the robot could cause harm to the patient that the robot is being used to operate on. Rather than the robot mimicking the commands associated with the moveable end portion being dropped, the robot would hold its position until the moveable hand portion 8 is reacquired by the operator and a button is pressed, for example, to confirm that the operator is ready to provide further commands for the robot.

The first wrist joint comprises a slip ring 14, a bearing 14, a magnet 24, a magnetism sensor 26 and first and second electrical conductors 21 and 22. Here these components are schematically represented in a simplified form. However, in reality, these components would be configured similarly to the wrist joint 6 shown in FIG. 5.

The electrical conductor 21 coupled at a first end to the rotor 15 of the first wrist joint 6a extend generally towards the static end portion 9. A second end of the first electrical conductor is coupled to a micro plug 39. Also coupled to the micro plug 39 is a first end of a first electrical conductor 21 comprised as part of the first elbow joint 7a. The micro plug 39 is adapted to electrically couple electrical conductors to one another and thereby facilitates the electrical coupling of the first wrist joint 6a to the first elbow joint 7a.

The first elbow joint 7a further comprises a bearing 18, a magnet 24, a magnetism sensor 26 and a second electrical conductor 22. Here these components are schematically represented in a simplified form. However, in reality, these components would be configured similarly to the elbow joint 7 shown in FIGS. 6a and 6b.

The second wrist joint 6b is configured similarly to the first wrist joint 6a and in accordance with the wrist joint 6 shown in FIG. 5. The second, third and fourth elbow joints 7b, 7c, 7d are configured similarly to the first elbow joint 7a and in accordance to the elbow joint 7 shown in FIGS. 10a and 10b. Further each joint is electrically coupled to its adjacent joint or joints via a combination of electrical conductors 21, 22 and micro plugs 39 similarly to the configuration set out above between the first wrist joint 6a and the first elbow joint 7a. Although, in some instances such as between the second wrist joint 6b and the second elbow joint 7b the electrical conductors 21, 22 and micro plugs 39 may be replaced by a PCB 38 serving the same function.

An advantage of using PCBs 38 is that each joint can be electrically coupled to an adjacent joint with a single electrical conductor (such as a cable). This simplifies the internal structure of the arm device 2 and allows easier assembly and maintenance.

Ultimately, the moveable end portion 8 is electrically coupled to the static end portion 9 via the various PCBs 38, electrical conductors 21, 22 and sliprings 14 comprised in the arm device. This allows electrical information to be transmitted from the moveable end portion 8 to the static end portion 9. For example, information relating to movement detected by the motion sensor 42 may be transmitted to the static end portion 9 and the associated master controller.

Further, electrical information may be transmitted from each joint 6a, 7a, 6b, 7b, 7c, 7d of the arm device 2 to the static end portion 9. For example, information relating to simultaneous rotation at each joint 6a, 7a, 6b, 7b, 7c, 7d may be detected by the respective magnetism sensors 26 and transmitted to the static end portion 9 and the associated master controller 100, 200. This allows complex movement commands, requiring several degrees of freedom, to be performed by the operator, continuously sensed by the arm device 2, transmitted to the master controller and carried about by the slave robot.

Referring now to FIG. 9, a close-up view of a moveable end portion 8 is shown. The moveable end portion 8 comprises a handle 40 that is ergonomically designed to be held comfortably in the hand of the operator and levers 46 that are configured to be readily manipulated by the operator using their first finger and thumb with a pinching motion.

Referring now to FIG. 10, the internal components of the moveable end portion 8 are revealed. The moveable end portion 8 further comprises a motion sensor 42 and a magnetism sensor 26 in accordance with FIG. 8. The moveable end portion also comprises a magnet (not shown) positioned in one of the levers 46. The magnetism sensor 26 is adapted to detect the magnet and particularly the distance between the magnetism sensor 26 and the magnet. The data measured by the magnetism sensor may be transmitted to the computer so that the position of the levers can be calculated. The positional information may be used by to issue corresponding instructions that are sent to a surgical instrument such as forceps.

The levers 46 are engageable with one another via a gear mechanism 47 which is shown more clearly in FIGS. 11a, 11b and 11c. The gear mechanism 47 ensures that the two levers 46 move symmetrically to one another. This means that movement of the levers mimics the symmetrical movement possible with the corresponding surgical instrument, thereby allowing the operator to control the surgical instrument more intuitively and with greater accuracy.

Referring now to FIG. 12, a master controller according to the second aspect of the invention is designated generally by the reference numeral 100. The master controller 100 comprises a pair of arm devices 2 according to an embodiment of the first aspect of the invention. Each arm device 2 comprises the same features as the arm device 2 shown in FIGS. 7 and 8, such as a universal joint 4 for example. The master controller further comprises a base 106 and a view port 104. The base 106 may be mounted on a platform, such as a desk or table, at a height suitable to allow an operator of the master controller 100 to operate the arm devices 2 and look into the view port 104 comfortably in order to control a robot (not shown), for example during a surgical procedure. The view port 104 may be configured to show video footage to aid the operator in controlling the robot. The video footage may be recorded by the slave robot itself or it may be recorded by an auxiliary instrument, such as an endoscope during a surgical procedure. The video footage may be transmitted to the master controller 100 so that it may be displayed in the view port 104 to provide a real-time view of the robot or from the robot's perspective.

The viewport 104 may comprises a display for each eye. Each display may be high-resolution and for example may comprise 1920×1080 pixels, therefore providing a combined resolution of 3840×2160 pixels.

Referring now to FIG. 13, a master controller 200 is shown which comprises a base 206 but not a view port. However, the arm devices 2 are the same as those shown in FIG. 12. Each arm device 2 therefore comprises a universal joint 4, which universal joint comprises two wrist joints 6 and an elbow joint 7. Each arm device further comprises three additional elbow joints 7, a moveable end portion 8 and a static end portion 9.

FIG. 3 shows the master controller 200 with each arm device 2 in a different positional configuration. Arm device 2a is positioned in a contracted configuration which would require the operator to hold the moveable end portion 8 close to their body. Arm devices 2b is positioned in an outstretched configuration for which the operator would be required to stretch their hand, holding the moveable end portion 8, away from their body. Each moveable end portion 8 comprises a handle 40 which the operator may grasp, allowing them to comfortably grip the moveable end portion 8. Each moveable end portion further comprises levers 46 which the operator may control with their first finger and thumb with a pinching motion. The levers 46 may provide the operator with an additional aspect of control over the robot, such as controlling forceps located at a distal end of a surgical robot.

Referring now to FIG. 15, a master controller 300 is shown which comprises a base 306 and a pair of arm devices 302 according to an embodiment of a first aspect of the invention. The majority of the features of the arm devices 302, such as the first wrist joint 6a, are equivalent to the corresponding features of the arm devices 2. However, the moveable end portion 308 is configured vertically such that the handle 340 extends substantially coaxially to the first axis of the first wrist joint 6a, rather than extending substantially normal to the first axis as is the case for the handle 40 in the moveable end portion 8 shown in FIGS. 9 to 14.

An advantage of this configuration is that, in use, the first and second elbow joints 7a and 7b have different neutral positions which reduce the likelihood of the first and second wrist joints 6a and 6b aligning with one another and potentially causing gimbal lock. A disadvantage of this configuration is that the operator's arms are more likely to interfere with the movement of the arm devices 302, thereby reducing the workspace which is available.

A master controller 100, 200, 300 according to an embodiment of the second aspect of the invention, forming part of a surgical device may be used to perform a minimally invasive surgical procedure. Accordingly FIG. 16 shows a surgical theatre in use that comprises a surgical device 528 which in turn comprises a master controller 100, an operating station 510, a control station 520, a robot 530 and an operating table 540.

A patient 502 may be positioned on the operating table 540. The robot 530, configured to perform the required endoscopy-typed procedure, may be suitably positioned relative to the patient 502. In this embodiment the robot 530 comprises a mounting unit 538 which may be mounted directly to the operating table 540 and allows the robot 530 to be appropriately positioned relative to the patient 502. Alternatively, the robot 530 may be configured to perform surgical procedures through keyhole-type incisions.

The robot 530 may further comprise an endoscope 532, a pair actuation packs 534 and a pair of snake-like surgical instruments 536 which are driven by the actuation packs 534. Each surgical instrument 536 may comprise a narrow body portion capable of snake-like movement with several degrees of freedom and a head portion adapted to provide a surgical tool such as forceps capable of opening and closing. The endoscope 532 may be positioned, through a natural orifice of key-hole incision, to record a view of the surgical instruments 563 inside the patient 502.

In this embodiment the master controller 100 comprises a pair of arm devices 2, a viewport 104 and a base 106 in accordance with the embodiment shown in FIG. 12. The base 106 may be mounted to the operating station 510 and particularly to a platform 512 forming part of the operating station 510. The platform 512 may be configured at a height suitable to allow a surgeon 504 to operate the arm devices 2 freely and comfortably. The surgeon 504 may position himself/herself, in front of the master controller 100 such that he may extend his arms over the controller base 106 and grasp a handle of each arm device 2 with corresponding hands. The surgeon 504 may grasp each handle such that the first finger and thumb of each hand are positioned in-line with the levers of the moveable end portion to allow him to control the levers with a pinching motion. The remaining fingers of each hand may be wrapped around the relevant handle. The surgeon 504 may use each arm device 2 to control a respective one of the surgical instruments 536.

In FIG. 16 the surgeon 504 is in a sitting position behind the master controller 100, but a standing position would also be possible if the platform 512 was raised appropriately. However the sitting position may be preferable to the surgeon 504 in this case as the master controller 100 further comprises a foot pedal 514 which allows the surgeon to provide additional instructions to the robot 530.

The surgeon 504 and master controller 100 may be positioned inside or outside of the surgical theatre occupied by the patient. In this embodiment the master controller 100 is non-sterile and must therefore be suitably positioned away from the patient 502.

The viewport 104 may be configured to display, in real-time, an image that is recorded by the endoscope 532. Therefore the surgeon 504 may further position himself relative to the master controller 100 so that he may look into the view port 104 while also maintaining control of the arm devices 2. This allows the surgeon 504 to watch how his manipulation of the arm devices 2 corresponds to movements of the surgical instruments 536 and thereby accurately perform the necessary surgical procedure.

In the embodiment shown in FIG. 16 the master controller 100 is coupled to an auxiliary screen 526 forming part of the control station 520. The auxiliary screen 526 allows other medical practitioners present for the surgery, such as a surgical nurse 506, to keep track of what stage the surgery is at. The surgical nurse 506 may be required to perform certain actions that cannot be performed remotely and/or to assist the surgeon in circumstances where physical intervention is required.

In other embodiments of the invention the master controller may not comprise a viewport and the auxiliary screen may be the only means for providing the surgeon a view of the surgical procedure. In such embodiments the auxiliary screen may be positioned in front of the surgeon so that the surgeon may easily view the screen while maintaining control of the arm devices. In some embodiments of the invention there may be a plurality of auxiliary screens including one for the lead surgeon and one for other medical practitioners participating in the surgery.

The control station 520 may further comprise an endoscope control unit 522 and a robot control unit 524. With a view of the surgical instruments 536, the surgeon 504 may move the moveable end portion of each arm device 2 in order to control a respective one of the robot's surgical instruments. In accordance with the embodiment of the invention shown in FIG. 8, the magnetism sensor 26 located in each joint of the arm device 2 may detect angular movement of the associated magnet 24 in response to the moveable end portion 8 being moved by the surgeon 504. The information recorded by the magnetism sensor 26 may be transmitted to the robot control unit, for example the information may be in the form of induced voltages which are transmitted along electrical conductors 21, 22 passing through each arm device 2. The robot control unit 524 may interpret the data recorded by the various magnetism sensors 26 and generate command signals that are transmitted to the robot 530, instructing the surgical instruments 536 to move such that the movement of each head portion corresponds to the movement of the respective moveable end portion controlled by the surgeon 504. The surgeon 504 may then watch the surgical instruments 536 mirror the movement of his hands in real time through the view port 104 or auxiliary screen 526.

Similarly, the surgeon may pinch or release the levers 46 of each moveable end portion 8, 308. Information relating to the position of the levers 46 may be transmitted to the robot control unit 524 such that corresponding instructions may be sent to the forceps of the surgical instruments 536.

Further, if the surgeon 504 were to accidentally drop the moveable end portions 8 the movement will be detected by the motion sensor 42 located in each moveable end portion 8. The robot control unit 524 may be configured to associate a movement that corresponds to acceleration due to gravity with the moveable end portion 8 being dropped. If such a motion is detected the robot control unit may override instructions for the surgical instrument 536 that would normally be associated with movement of the moveable end portion 8 and instead instruct the surgical instruments 536 to maintain the position that was last instructed, before the drop was recorded.

This reduces the risk of the robot 530 performing movements that were not intended by the surgeon 504 which could be harmful to the patient 502.

As an additional safety precaution a technical engineer 508 may also be present during the surgical procedure. The technical engineer would be capable of responding to any technical issues associated with the master controller 100, controlling station 520 or robot 530.

The invention claimed is:

1. An arm device, comprising:
 a universal joint, which universal joint comprises a first wrist joint, a second wrist joint and a first elbow joint, wherein:
  the first wrist joint and the second wrist join each comprise:
   a first part,
   a second part, and
   a slipring, the slipring comprising:
    a rotor coupled to the first part, and
    a stator coupled to the second part,
     wherein the rotor is coaxially engageable with the stator and infinitely rotatable relative to the stator such that the first part of the first wrist joint is infinitely rotatable relative to the second part of the first wrist joint about a first axis, and the first part of the second wrist joint is infinitely rotatable relative to the second part of the second wrist joint about a second axis;
  the first elbow joint comprises:
   a first portion, and
   a second portion,
    wherein the first portion is rotatably engageable with the second portion about a third axis;
    the first wrist joint is coupled to the first elbow joint;
    first elbow joint is coupled to the second wrist joint; and
    the second axis intersects the first axis at an intersection point and the third axis intersects the first axis and the second axis at the intersection point.

2. An arm device according to claim 1, wherein the arm device further comprises:
 at least one additional elbow joint, wherein
  at least one additional elbow joint comprises:
   a first portion, and
   a second portion,
    wherein the first portion is rotatably engageable with the second portion about an additional axis; and
  each at least one additional elbow joint is coupled to the universal joint.

3. An arm device according to claim 1, wherein the arm device further comprises:
 at least one additional wrist joints, wherein
  each at least one additional wrist joint comprises:
   a first part,
   a second part, and
   a slipring, the slipring comprising:
    a rotor coupled to the first part, and
    a stator coupled to the second part,
     wherein the rotor is coaxially engageable with the stator and infinitely rotatable relative to the stator such that the first part is infinitely rotatable relative to the second part about an additional axis; and
  each at least one additional wrist joint is coupled to the universal joint.

4. An arm device according to claim 1, wherein the first part of each of the first wrist joint and the second wrist joint is rotatably engageable with the second part of the corresponding wrist joint.

5. An arm device according to claim 4, wherein each of the first wrist joint and the second wrist joint further comprises;
 a bearing, the bearing having an inner surface and an outer surface, wherein
  the inner surface is rotatable relative to the outer surface and engageable with the first part of the wrist joint, and
  the outer surface is engageable with the second part of the wrist joint such that the first part is rotatably engageable with the second part via the bearing.

6. An arm device according to claim 1, wherein the first part of each of the first wrist joint and the second wrist joint is electrically coupled to the second part of that wrist joint via the slipring.

7. An arm device according to claim 1, wherein each of the first wrist joint and the second wrist joint comprises:
 a first electrical conductor coupled to the rotor; and
 a second electrical conductor coupled to the stator, wherein the first electrical conductor is electrically coupled to the second electrical conductor via the slipring.

8. An arm device according to claim 1, wherein each of the first wrist joint and the second wrist joint further comprises:
a wrist joint sensor configured to measure an angle of rotation of the respective wrist joint.

9. An arm device according to claim 7, wherein the wrist joint sensor comprises:
a magnet coupled to the rotor of the respective wrist joint, and
a magnetism sensor fixed relative to the stator of the respective wrist joint and adapted to detect the magnet.

10. An arm device according to claim 9, wherein the magnet is coupled to a distal end of the corresponding rotor and the first electrical conductor is coupled to a proximal end of the rotor.

11. An arm device according to claim 2, wherein the first elbow joint and each at least one additional elbow joint further comprises an elbow joint sensor configured to measure an angle of rotation of the respective elbow joint.

12. An arm device according to claim 11, wherein the elbow joint sensor comprises:
a magnet fixed relative to the first portion of the respective elbow joint, and
a magnetism sensor fixed relative to the second portion of the respective elbow joint and adapted to detect the magnet.

13. An arm device according to claim 9, wherein the magnet corresponding to at least one of the first wrist joint or the second wrist joint is diametrically magnetized.

14. An arm device according to claim 9, wherein the magnetism sensor corresponding to at least one of the first wrist joint or the second wrist joint comprises one of a Hall effect sensor or a magnetometer.

15. An arm device according to claim 1, wherein the arm device further comprises:
a static end portion located at a proximal end of the arm device, and
a moveable end portion located at a distal end of the arm device,
wherein the moveable end portion is electrically coupled to the static end portion via any one or more of the first wrist joint, the second wrist joint, or the first elbow joint.

16. An arm device according to claim 15, wherein the moveable end portion comprises a motion sensor.

17. An arm device according to claim 16, wherein the motion sensor comprises an accelerometer.

18. A wrist joint, which forms part of an arm device according to claim 1, the wrist joint comprising:
a first part;
a second part;
a magnet;
a magnetism sensor; and
a slipring, the slipring comprising:
a rotor coupled to the first part, and
a stator coupled to the second part,
which wherein the rotor is coaxially engageable with the stator and infinitely rotatable relative to the stator, and
the magnet is coupled to the rotor; and the magnetism sensor is fixed relative to the stator and is adapted to detect the magnet.

19. A surgical device comprising a robot and a master controller, the master controller comprising:
a base; and
an arm device according to claim 1,
wherein the arm device extends from the base.

* * * * *